United States Patent
Rampton et al.

(10) Patent No.: US 12,094,108 B2
(45) Date of Patent: Sep. 17, 2024

(54) LYMPH NODE DETECTION SYSTEM AND METHODS FOR USE

(71) Applicant: SANFORD HEALTH, Sioux Falls, SD (US)

(72) Inventors: Joshua Rampton, Bismarck, ND (US); Andrew Miller, Bismarck, ND (US); John Miller, Bismarck, ND (US)

(73) Assignee: Sanford Health, Sioux Falls, SD (US)

( * ) Notice: Subject to any disclaimer, the term of this patent is extended or adjusted under 35 U.S.C. 154(b) by 732 days.

(21) Appl. No.: 17/262,909

(22) PCT Filed: Sep. 12, 2019

(86) PCT No.: PCT/US2019/050766
§ 371 (c)(1),
(2) Date: Jan. 25, 2021

(87) PCT Pub. No.: WO2020/056101
PCT Pub. Date: Mar. 19, 2020

(65) Prior Publication Data
US 2021/0256697 A1 Aug. 19, 2021

Related U.S. Application Data

(60) Provisional application No. 62/730,347, filed on Sep. 12, 2018.

(51) Int. Cl.
*G06T 7/00* (2017.01)
*G16H 30/20* (2018.01)

(52) U.S. Cl.
CPC .......... *G06T 7/0012* (2013.01); *G16H 30/20* (2018.01); *G06T 2207/10081* (2013.01)

(58) Field of Classification Search
CPC ......... G06T 7/0012; G06T 2207/10081; G06T 2207/30101; G16H 30/20
See application file for complete search history.

(56) References Cited

U.S. PATENT DOCUMENTS

2008/0317314 A1   12/2008  Schwartz et al.
2012/0041685 A1*  2/2012   Ding .................... A61N 5/1031
                                                                 702/19

(Continued)

OTHER PUBLICATIONS

The International Search Report (ISR) with Written Opinion for PCT/US2019/050766 dated Jan. 23, 2020, pp. 1-17.

(Continued)

*Primary Examiner* — Christopher M Brandt
(74) *Attorney, Agent, or Firm* — McDonnell Boehnen Hulbert & Berghoff LLP

(57) ABSTRACT

The disclosure provides example methods and a non-transitory computer-readable medium that has stored thereon program instructions that upon execution by a processor, cause performance of a set of acts including: (a) receiving a digital image, where the image comprises a plurality of voxels, (b) selecting from the plurality of voxels at least one voxel corresponding to soft tissue cells, (c) expanding the selected voxels to include adjacent voxels until an endpoint voxel is identified, (d) determining whether the expanded selected voxels indicate a presence of a soft tissue body, and (e) in response to a determination that the expanded selected voxels indicate the presence of the soft tissue body, associating the digital image with a database of digital images showing soft tissue bodies.

20 Claims, 13 Drawing Sheets

(56) References Cited

U.S. PATENT DOCUMENTS

2019/0012805 A1\* 1/2019 Bertram .................... G06T 7/74
2019/0370970 A1\* 12/2019 Kim ..................... G06T 7/0016

OTHER PUBLICATIONS

Barbu, Adrian et al. "Automatic Detection and Segmentation of Lymph Nodes From CT Data" IEEE Transactions on Medical Imaging (2012) vol. 31(2), pp. 240-250.

\* cited by examiner

LYMPH NODE DETECTION SYSTEM AND METHODS FOR USE

CROSS-REFERENCE TO RELATED APPLICATIONS

This application is a U.S. national phase of International Application No. PCT/US2019/050766, filed on Sep. 12, 2019, which claims priority to U.S. Provisional Application No. 62/730,347, filed Sep. 12, 2018, both of which are incorporated by reference herein in their entirety

BACKGROUND

Known methods to detect lymph nodes from CT images include a random forest statistical classifier, a local intensity structure analyses based on a Hessian matrix, or a radial structure tensor. Detection of lymph nodes can be an important clinical diagnostic tool but is very challenging due to the low contrast of surrounding structures in CT images and due to lymph nodes' varying sizes, poses, shapes and sparsely distributed locations.

BACKGROUND

Known methods to detect lymph nodes from CT images include a random forest statistical classifier, a local intensity structure analyses based on a Hessian matrix, or a radial structure tensor. Detection of lymph nodes can be an important clinical diagnostic tool but is very challenging due to the low contrast of surrounding structures in CT images and due to lymph nodes' varying sizes, poses, shapes and sparsely distributed locations.

SUMMARY

In a first aspect, an example non-transitory computer-readable medium is disclosed. The computer readable medium has stored thereon program instructions that upon execution by a processor, cause performance of a set of acts including: (a) receiving a digital image, wherein the image comprises a plurality of voxels, (b) selecting from the plurality of voxels at least one voxel corresponding to soft tissue cells, (c) expanding the selected voxels to include adjacent voxels until an endpoint voxel is identified, (d) determining whether the expanded selected voxels indicate a presence of a soft tissue body, and (e) in response to a determination that the expanded selected voxels indicate the presence of the soft tissue body, associating the digital image with a database of digital images showing soft tissue bodies.

In a second aspect, an example method of detecting pathologic lymph nodes is disclosed. The method includes (a) receiving, via a computing device, a digital image, wherein the image comprises a plurality of voxels, (b) selecting, via the computing device, at least one voxel relating to soft tissue cells, (c) expanding, via the computing device, the selected voxels to include adjacent voxels until an endpoint voxel is identified, (d) determining, via the computing device, whether the expanded selected voxels indicate a presence of a soft tissue body, and (e) based on a determination that the expanded selected voxels indicate the presence of the soft tissue body, associating, by the computing device, the digital image with a database of digital images showing soft tissue bodies.

In a third aspect, an example non-transitory computer-readable medium is disclosed. The computer readable medium has stored thereon program instructions that upon execution by a processor, cause performance of a set of acts including: (a) receiving a digital image, wherein the digital image comprises a plurality of voxels, (b) selecting from the plurality of voxels at least one voxel corresponding to a bone cell, (c) expanding the selected voxels to include adjacent voxels until an endpoint voxel is identified, (d) determining whether the expanded selected voxels indicate a presence of a bone, and (e) in response to a determination that the expanded selected voxels indicate the presence of the bone, associating the digital image with a database of digital images showing bones.

In a fourth aspect, an example method of detecting bone metastasis is disclosed. The method includes: (a) receiving, via a computing device, a digital image, wherein the digital image comprises a plurality of voxels, (b) selecting, via the computing device, at least one voxel relating to a bone cell, (c) expanding, via the computing device, the selected voxels to include adjacent voxels until an endpoint voxel is identified, (d) determining, via the computing device, whether the expanded selected voxels indicate a presence of a bone, and (e) based on a determination that the expanded selected voxels indicate the presence of the bone, associating, by the computing device, the digital image with a database of digital images showing bones.

In a fifth aspect, an example non-transitory computer-readable medium is disclosed. The computer readable medium has stored thereon program instructions that upon execution by a processor, cause performance of a set of acts including: (a) receiving a digital image, wherein the digital image comprises a plurality of voxels, (b) identifying at least one vascular structure within the plurality of voxels, (c) excluding the at least one vascular structure from the plurality of voxels, (d) selecting from the plurality of voxels at least one voxel corresponding to a soft tissue cell, (e) expanding the selected voxels to include adjacent voxels until an endpoint voxel is identified, (f) determining whether the expanded selected voxels indicate a presence of a soft tissue body, and (g) in response to a determination that the expanded selected voxels indicate the presence of the soft tissue body, associating the digital image with a database of digital images showing soft tissue bodies.

In a sixth aspect, an example method of detecting pancreatic masses is disclosed. The method includes: (a) receiving, via a computing device, a digital image, wherein the digital image comprises a plurality of voxels, (b) identifying at least one vascular structure within the plurality of voxels, (c) excluding the at least one vascular structure from the plurality of voxels, (e) selecting, via the computing device, at least one voxel relating to a soft tissue cell, (f) expanding, via the computing device, the selected voxels to include adjacent voxels until an endpoint voxel is identified, (g) determining, via the computing device, whether the expanded selected voxels indicate a presence of pathologic cells, and (h) based on a determination that the expanded selected voxels indicate the presence of a soft tissue body, associating, by the computing device, the digital image with a database of digital images showing soft tissue bodies.

The features, functions, and advantages that have been discussed can be achieved independently in various examples or may be combined in yet other examples further details of which can be seen with reference to the following description and drawings.

Figure 1:
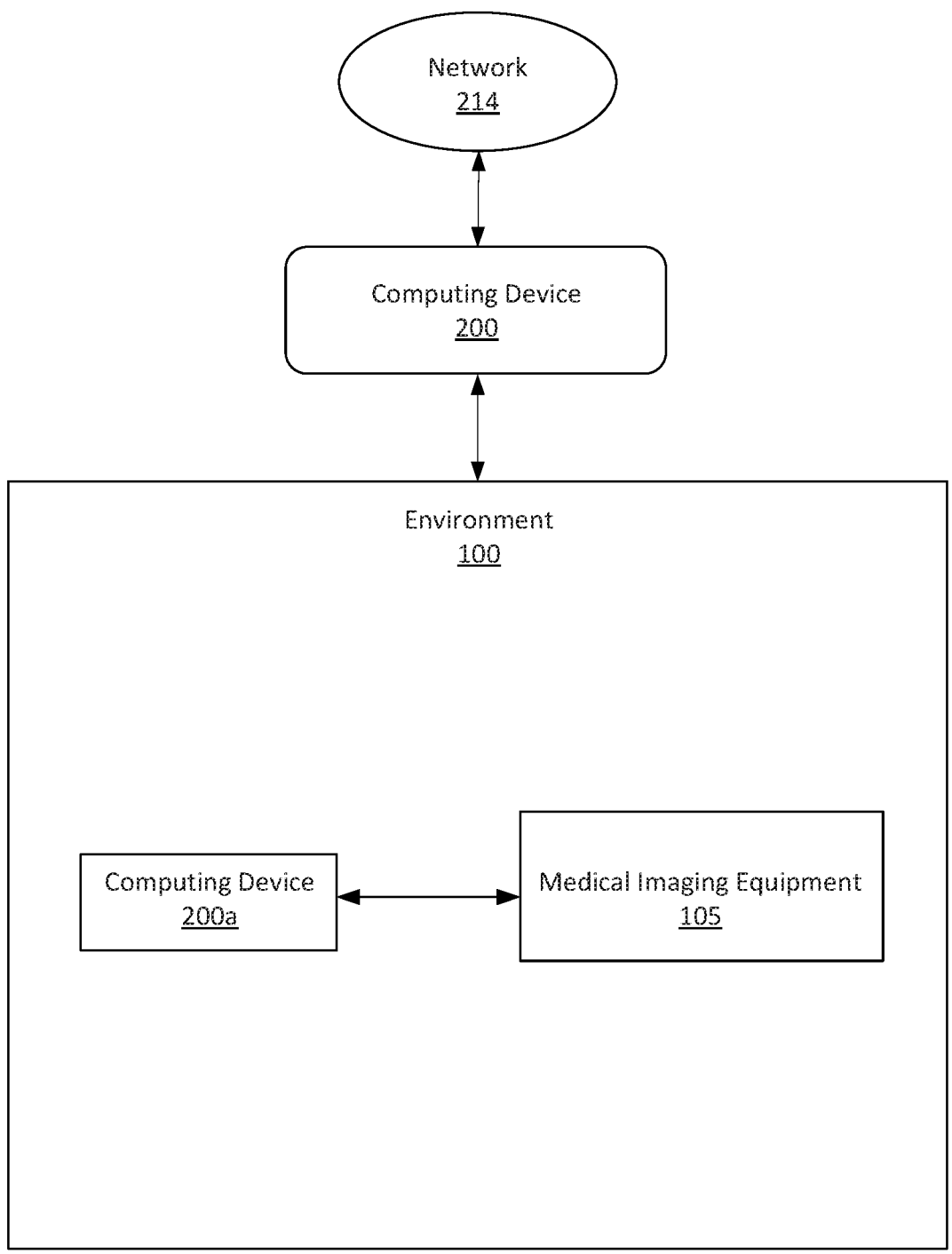
FIG. 1 is a functional block diagram of a system, according to one example implementation.

The drawings are for the purpose of illustrating examples, but it is understood that the inventions are not limited to the arrangements and instrumentalities shown in the drawings.

DETAILED DESCRIPTION

I. Overview

Embodiments of the non-transitory, computer readable medium and methods described herein can be used to beneficially provide medical personnel with a system to automatically detect lymph nodes, bony lesions, and pancreatic masses, for example, that have a high likelihood of pathology. The disclosed example non-transitory, computer readable medium and methods also advantageously allow medical personnel to perform quality control on their initial review of digital images of the neck, thoracic, abdomen, pelvis, and abdominoperineal regions, as well as digital images of an axial or appendicular skeleton. This system may also beneficially prioritize particular images by presenting images that have a high likelihood of pathology to medical personnel before images that do not have a high likelihood of pathology, thereby increasing accuracy and efficiency of digital image review.

As used herein, with respect to measurements, "about" means +/−5%.

As used herein, "DICOM compliant image" refers to an image that satisfies the DICOM standard set forth by the DICOM Standards Committee. The DICOM standard is also known as NEMA standard PS3, and ISO standard 12052: 2017 "Health informatics—Digital imaging and communication in medicine (DICOM) including workflow and data management."

As used herein, "soft tissue cells" refer to tissue cells that support and surround organs and specific tissues in the body that typically have defined borders.

As used herein, "soft tissue body" refers to organs and specific tissues in the body that have defined borders.

As used herein, "pathologic lymph node" refers to a lymph node with a high likelihood of pathology thereby indicating an increased potential for a deviation from a healthy, normal, or efficient condition, for example.

As used herein, "endpoint voxel" refers to the voxels that form the border of the potentially pathologic lymph node.

As used herein, "expanded selected voxels" refers to a potentially pathologic lymph node object in a digital image.

As used herein, an "indicator" refers to a marker that is configured to direct medical personnel's attention to a particular set of expanded selected voxels. The indicator may be a flag, annotation, asterisk, arrow, letter, or any other suitable symbol in a contrasting color with the underlying image or an animation that flashes or blinks, for example. The indicator may also include coloring the particular set of expanded voxels in a contrasting color with the underlying image.

As used herein, "surrounding voxels" refers to voxels adjacent to each endpoint voxel for a particular set of expanded selected voxels.

As used herein, "margination" refers to the voxel classification (e.g., bone, fat, branched object, etc.) of the surrounding cells to the endpoint voxel.

As used herein, a "cluster of expanded selected voxels" refers to a plurality of potentially pathologic lymph nodes in close proximity to one another (e.g., less than about 12 cm).

As used herein, a "branched object" refers to three or more areas of the image that lack defined borders, where the three or more areas exist on the same plane.

As used herein, "6-connectivity" means as sharing a common face with a selected voxel.

As used herein, "18-connectivity" means sharing a common edge with a selected voxel.

As used herein, "26-connectivity" means sharing a common vertex with a selected voxel.

II. Example Architecture

FIG. 1 is a block diagram showing an environment 100 that includes or involves, for example, medical imaging equipment 105 and described below. Methods 300, 400 and 500 in FIGS. 3-5 described below shows an embodiment of a method that can be implemented within this environment 100.

Figure 2:
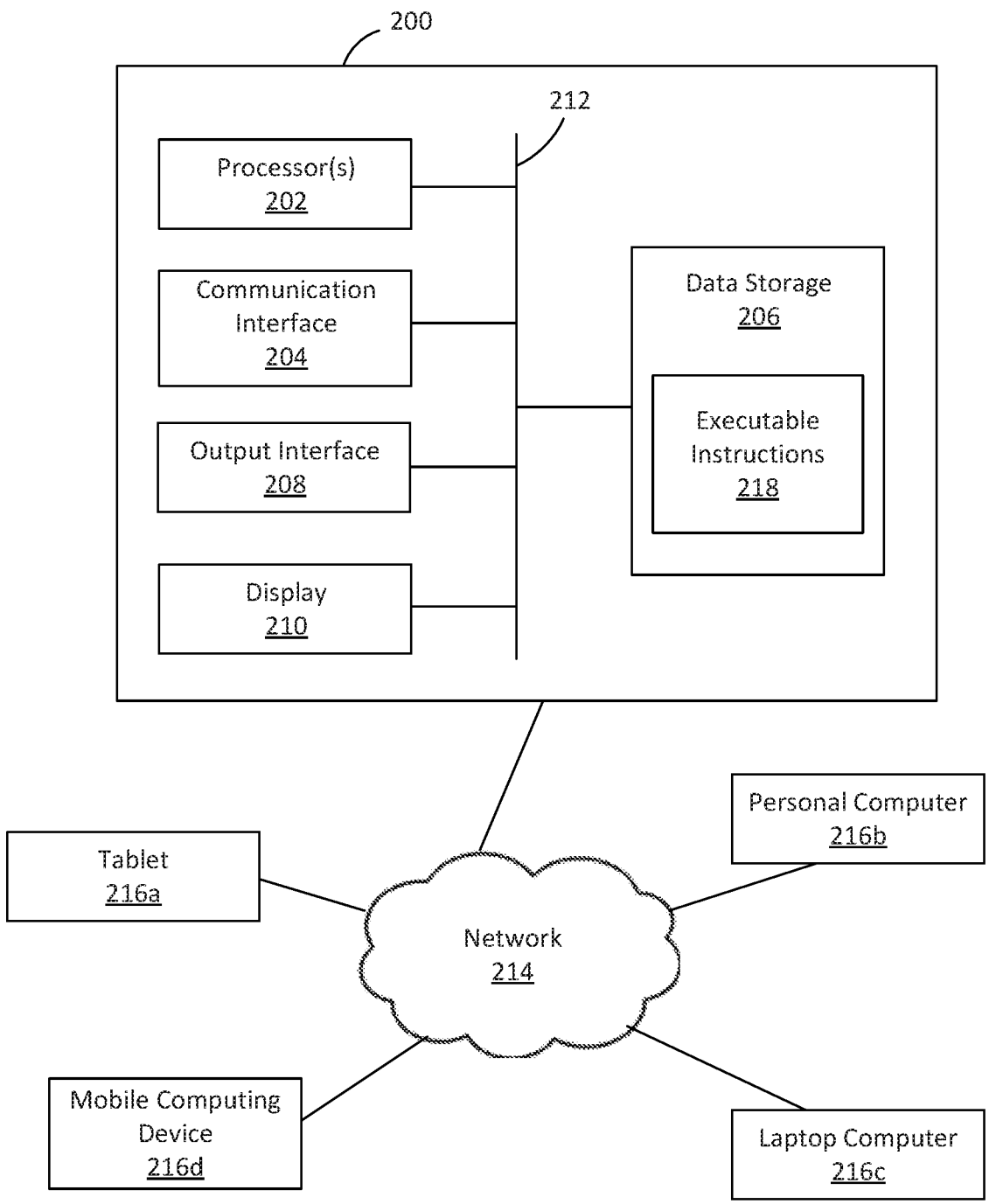
FIG. 2 depicts a block diagram of a computing device and a computer network, according to an example implementation.

FIG. 2 is a block diagram illustrating an example of a computing device 200, according to an example implementation, that is configured to interface with environment 100, either directly or indirectly. The computing device 200 may be used to perform functions of the methods shown in FIGS. 3-5 and described below. In particular, computing device 200 can be configured to perform one or more functions, including determining whether the expanded selected voxels indicate a presence of a soft tissue body, bone and/or pathologic cells and, based on that determination, modifying the image to include indications of the soft tissue body, the bone and/or the pathologic cells, for example. The computing device 200 has a processor(s) 202, and also a communication interface 204, data storage 206, an output interface 208, and a display 210 each connected to a communication bus 212. The computing device 200 may also include hardware to enable communication within the computing device 200 and between the computing device 200 and other devices (e.g. not shown). The hardware may include transmitters, receivers, and antennas, for example.

The communication interface 204 may be a wireless interface and/or one or more wired interfaces that allow for both short-range communication and long-range communication to one or more networks 214 or to one or more remote computing devices 216 (e.g., a tablet 216a, a personal computer 216b, a laptop computer 216c and a mobile computing device 216d, for example). For example, the term "network" as used herein contemplates cloud-based services that include Amazon Web Services ("AWS"), and Amazon SageMaker, IBM Watson Studio, IBM Watson Machine Learning, Google Cloud Machine Learning Engine, Azure Machine Learning Studio, TensorFlow, Pega Platform, Azure Machine Learning, Salesforce Einstein, Deep Cognition, BP Logix BPMS, Oracle Data Science Cloud Service, Azure Batch AI, IBM Watson Knowledge Studio, Box Skills, Peak, Infosys Nia, Playment, Artivatic, Ayasdi, Cogito Studio, DigitalGenius, Gluru AI, Google Cloud AI Hub, for example. Such wireless interfaces may provide for communication under one or more wireless communication protocols, such as Bluetooth, WiFi (e.g., an institute of electrical and electronic engineers (IEEE) 802.11 protocol), Long-Term Evolution (LTE), cellular communications, near-field communication (NFC), and/or other wireless communication protocols. Such wired interfaces may include Ethernet interface, a Universal Serial Bus (USB) interface, or similar interface to communicate via a wire, a twisted pair of wires, a coaxial cable, an optical link, a fiber-optic link, or other physical connection to a wired network. Thus, the communication interface 204 may be configured to receive input data from one or more devices, and may also be configured to send output data to other devices.

The communication interface 204 may also include a user-input device, such as a keyboard, a keypad, a touch screen, a touch pad, a computer mouse, a track ball and/or other similar devices, for example.

The data storage 206 may include or take the form of one or more computer-readable storage media that can be read or accessed by the processor(s) 202. The computer-readable storage media can include volatile and/or non-volatile storage components, such as optical, magnetic, organic or other memory or disc storage, which can be integrated in whole or in part with the processor(s) 202. The data storage 206 is considered non-transitory computer readable media. In some examples, the data storage 206 can be implemented using a single physical device (e.g., one optical, magnetic, organic or other memory or disc storage unit), while in other examples, the data storage 206 can be implemented using two or more physical devices.

The data storage 206 thus is a non-transitory computer readable storage medium, and executable instructions 218 are stored thereon. The instructions 218 include computer executable code. When the instructions 218 are executed by the processor(s) 202, the processor(s) 202 are caused to perform functions. Such functions include, but are not limited to, determining whether the expanded selected voxels indicate a presence of a soft tissue body, bone and/or pathologic cells and, based on that determination, modifying the image to include indications of the soft tissue body, the bone and/or the pathologic cells, for example.

The processor(s) 202 may be a general-purpose processor or a special purpose processor (e.g., digital signal processors, application specific integrated circuits, etc.). The processor(s) 202 may receive inputs from the communication interface 204, and process the inputs to generate outputs that are stored in the data storage 206 and output to the display 210. The processor(s) 202 can be configured to execute the executable instructions 218 (e.g., computer-readable program instructions) that are stored in the data storage 206 and are executable to provide the functionality of the computing device 200 described herein.

The output interface 208 outputs information to the display 210 or to other components as well. Thus, the output interface 208 may be similar to the communication interface 204 and can be a wireless interface (e.g., transmitter) or a wired interface as well. The output interface 208 may send commands to one or more controllable devices, for example The computing device 200 shown in FIG. 2 may also be representative of a local computing device 200a in environment 100, for example, in communication with medical imaging equipment 105. This local computing device 200a may perform one or more of the steps of the methods 300, 400, 500 described below, may receive input from a user and/or may send image data and user input to computing device 200 to perform all or some of the steps of methods 300, 400, 500.

Figure 3:
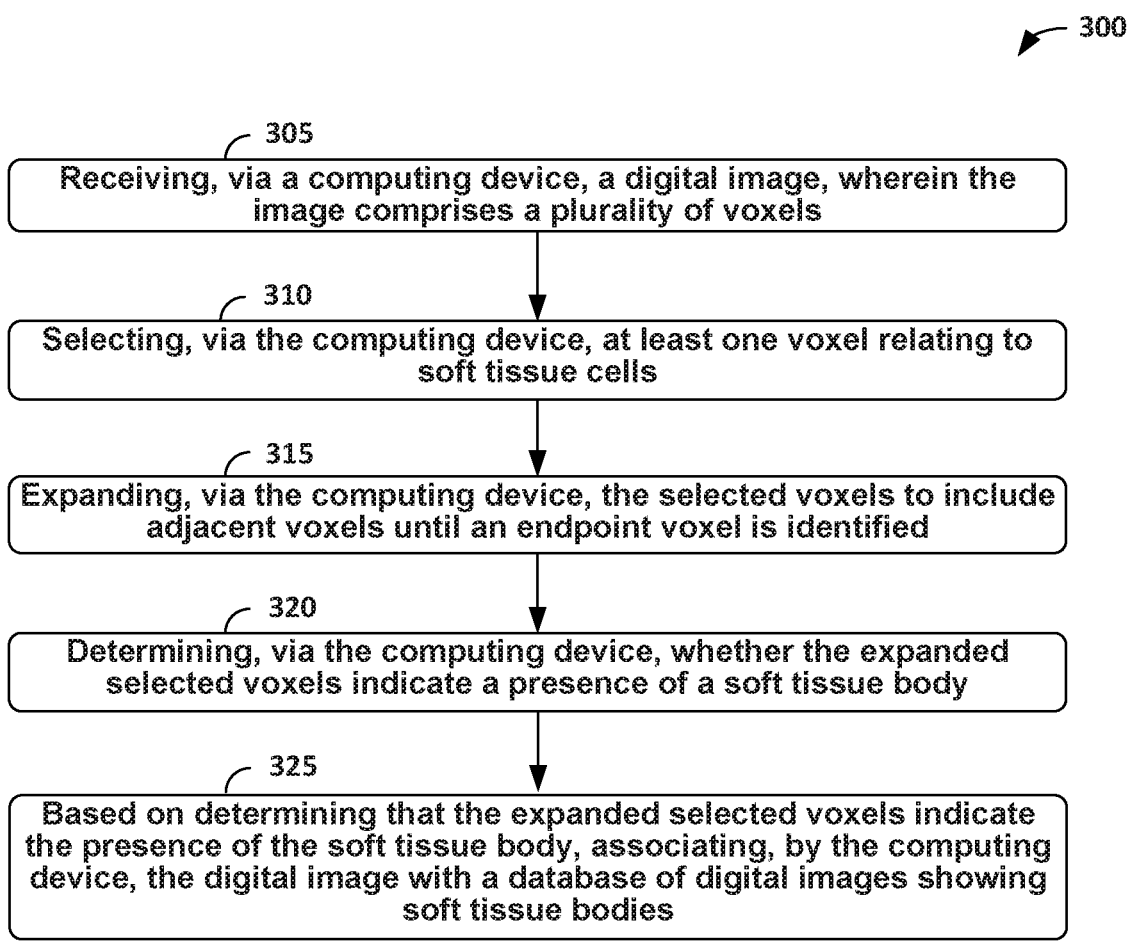
FIG. 3 shows a flowchart of a method, according to an example implementation.
Figure 4:
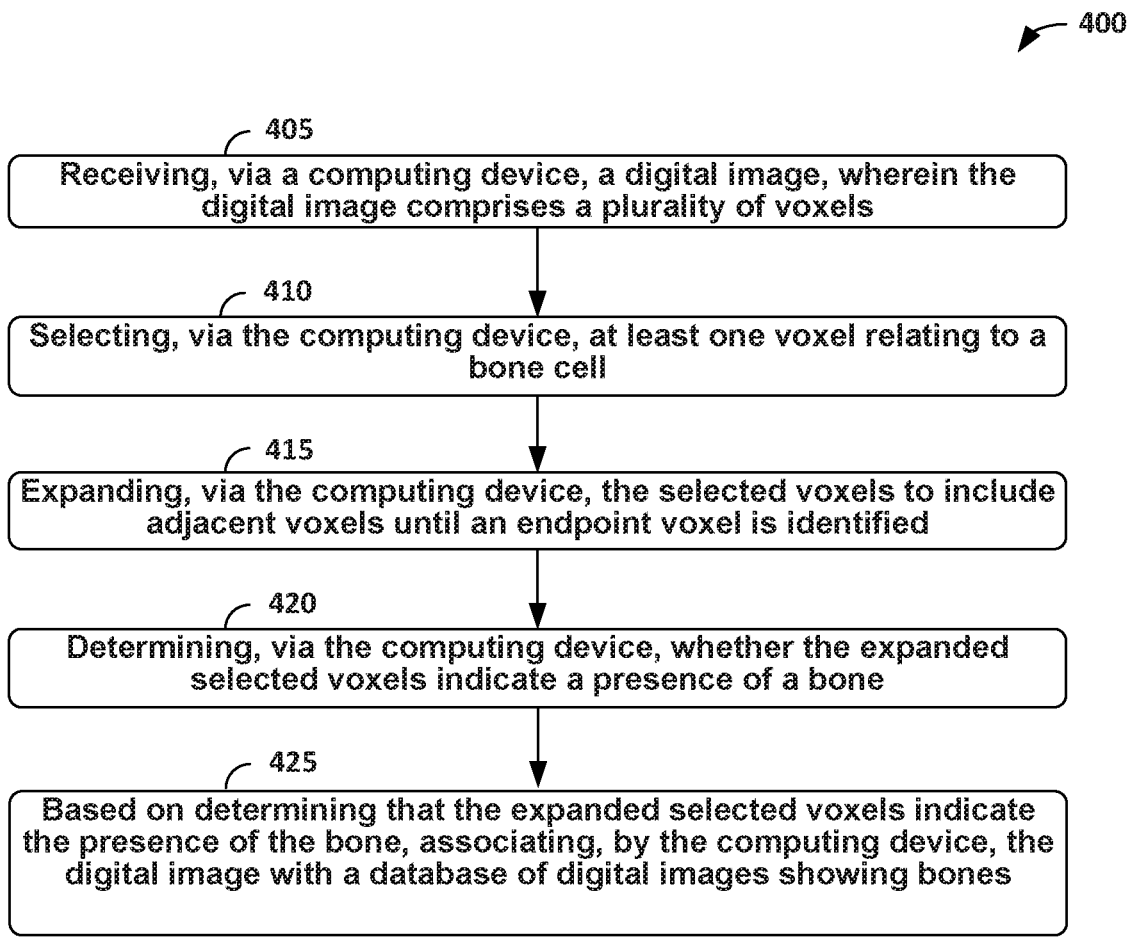
FIG. 4 shows a flowchart of a method, according to an example implementation.
Figure 5:
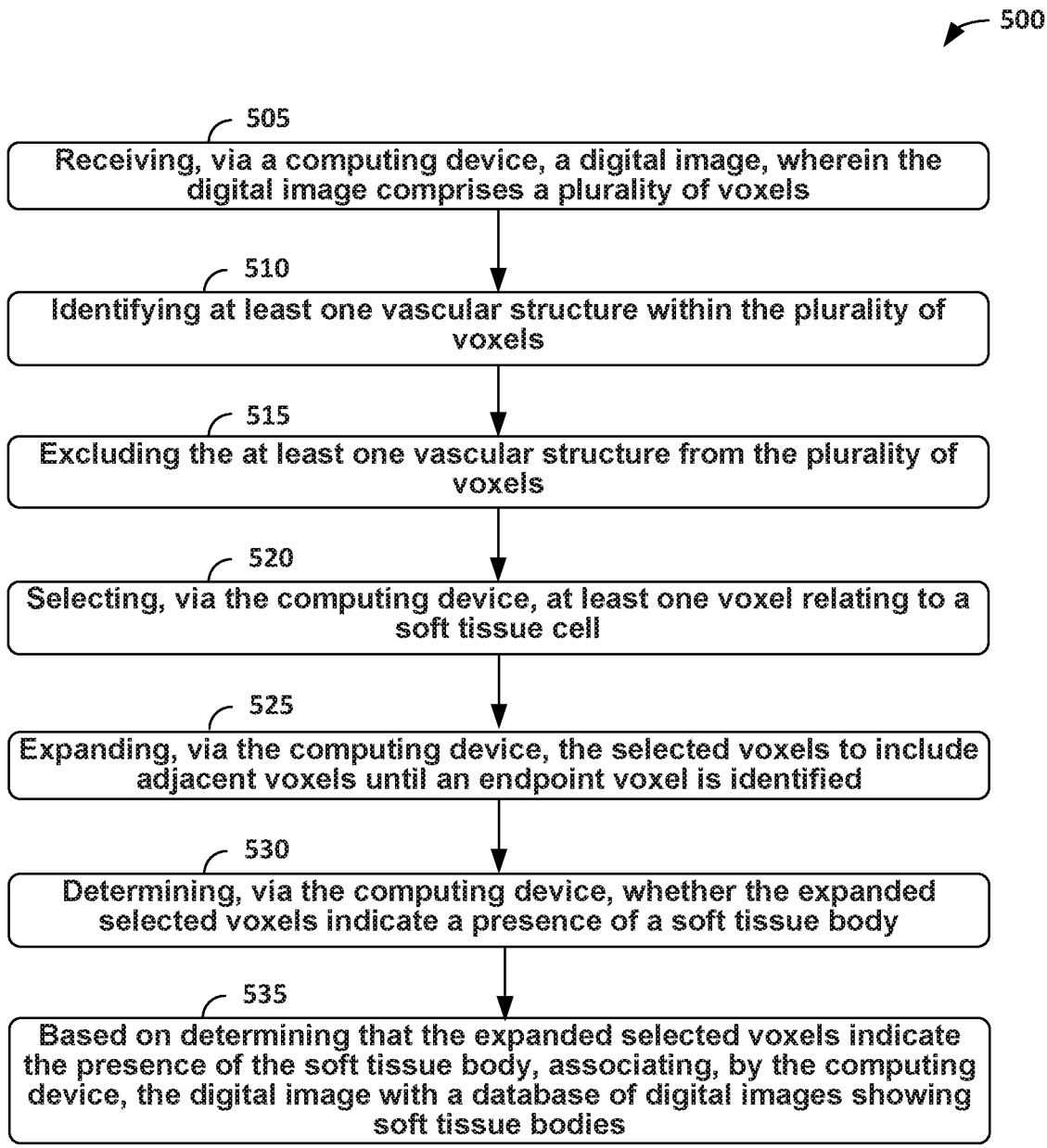
FIG. 5 shows a flowchart of a method, according to an example implementation.
Figure 6:
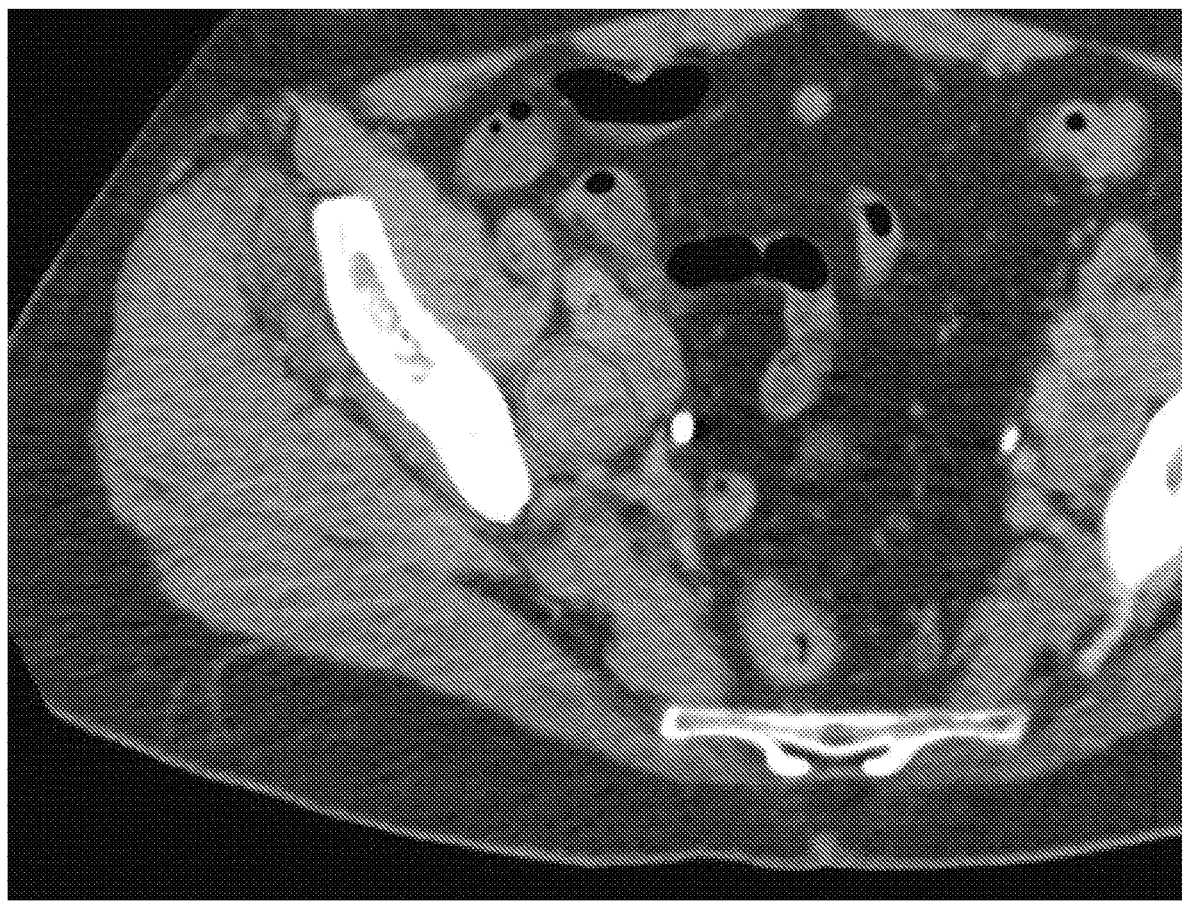
FIG. 6 shows a sample CT image of a patient's pelvis that depicts a lymph node (defined by the circle) that is marginated by fat, an iliac artery (defined by the "A" annotation), and an iliac vein (defined by the "V" annotation)
Figure 7:
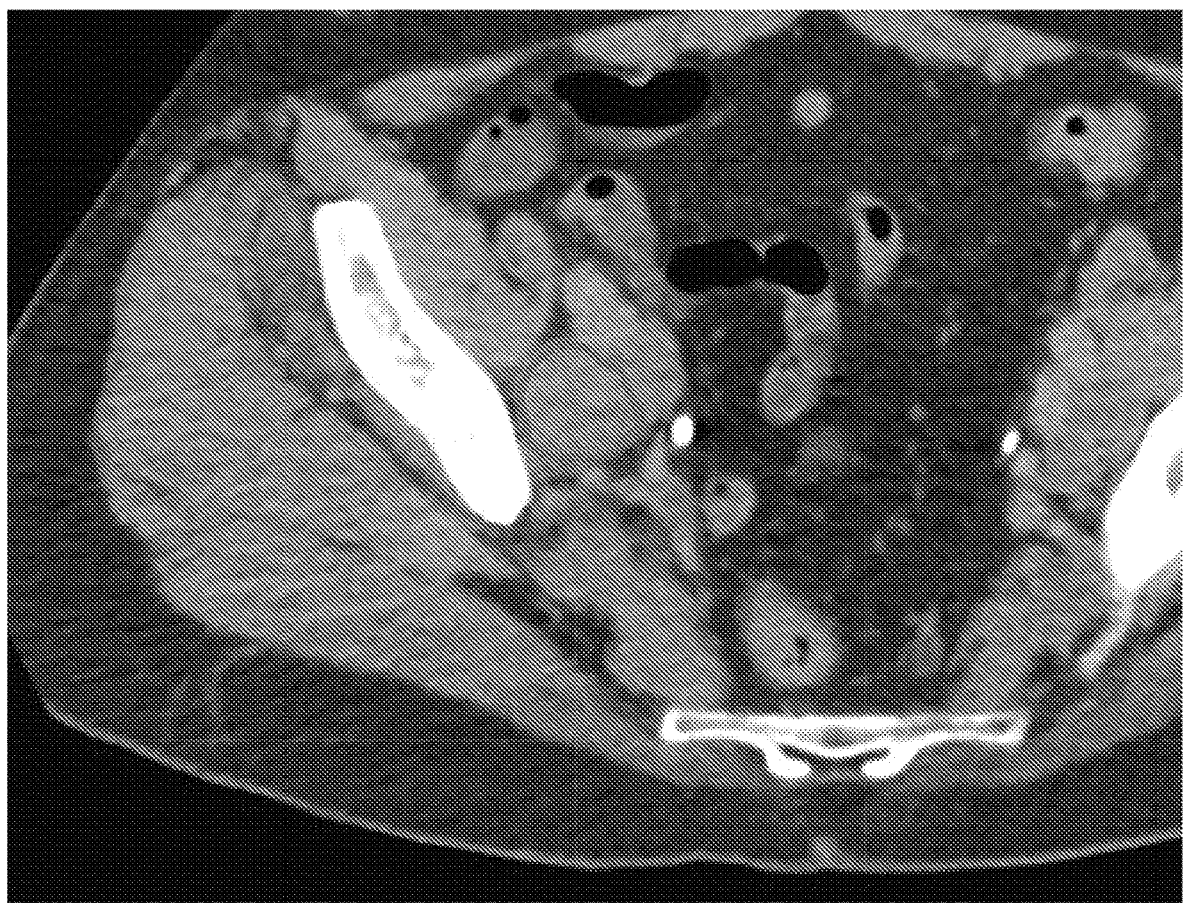
FIG. 7 shows a sample CT image of a patient's pelvis that depicts a lymph node that is marked by a circle as having a high likelihood of pathology.
Figure 8:
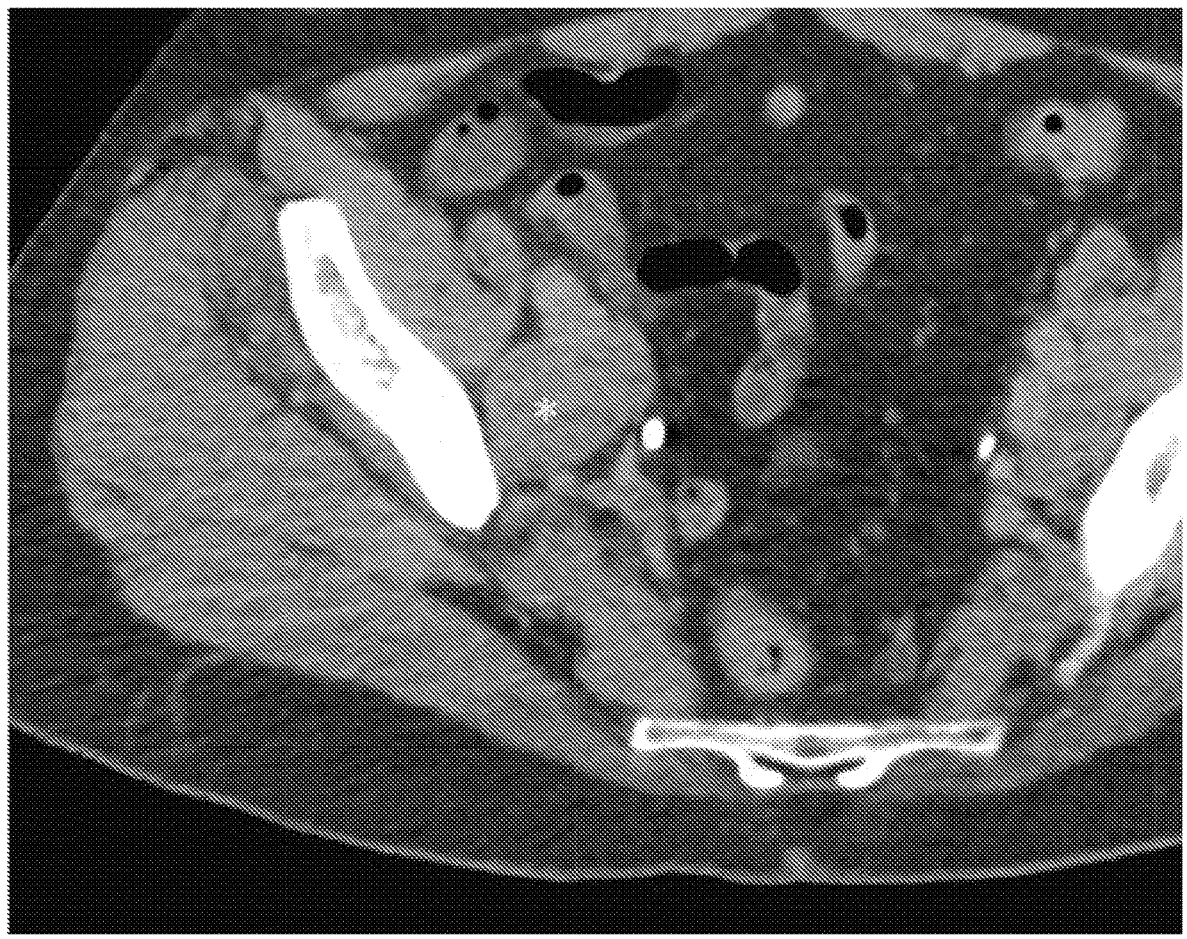
FIG. 8 shows a sample CT image of a patient's pelvis that depicts a lymph node that is marked by an asterisk as having a high likelihood of pathology.
Figure 9:
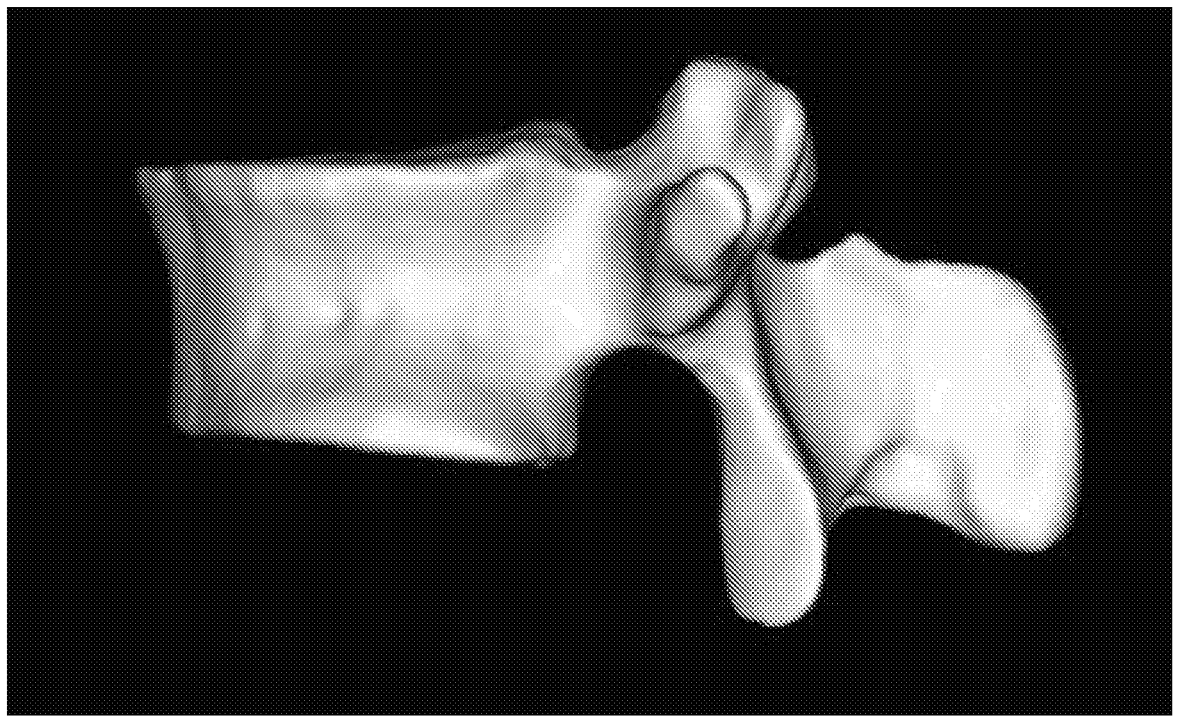
FIG. 9 shows a sample surface-shaded 3D projection from cortical voxels of a simulated human L1 vertebra.
Figure 10:
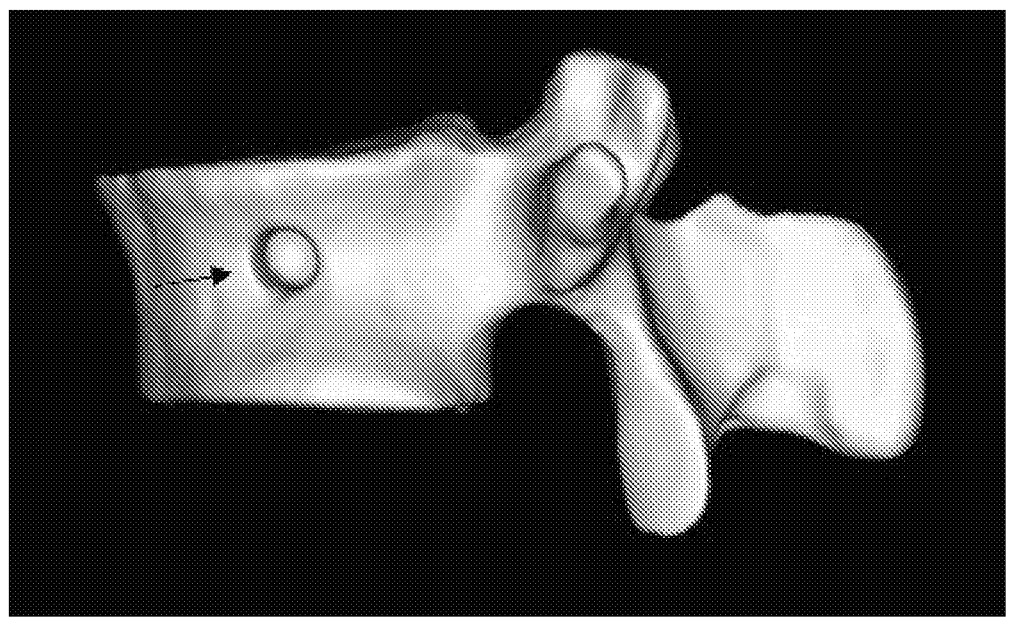
FIG. 10 shows a sample surface-shaded 3D projection from cortical voxels of a simulated L1 human vertebra. A lytic lesion is indicated by an arrow creating a free edge of non-cortical voxels.
Figure 11:
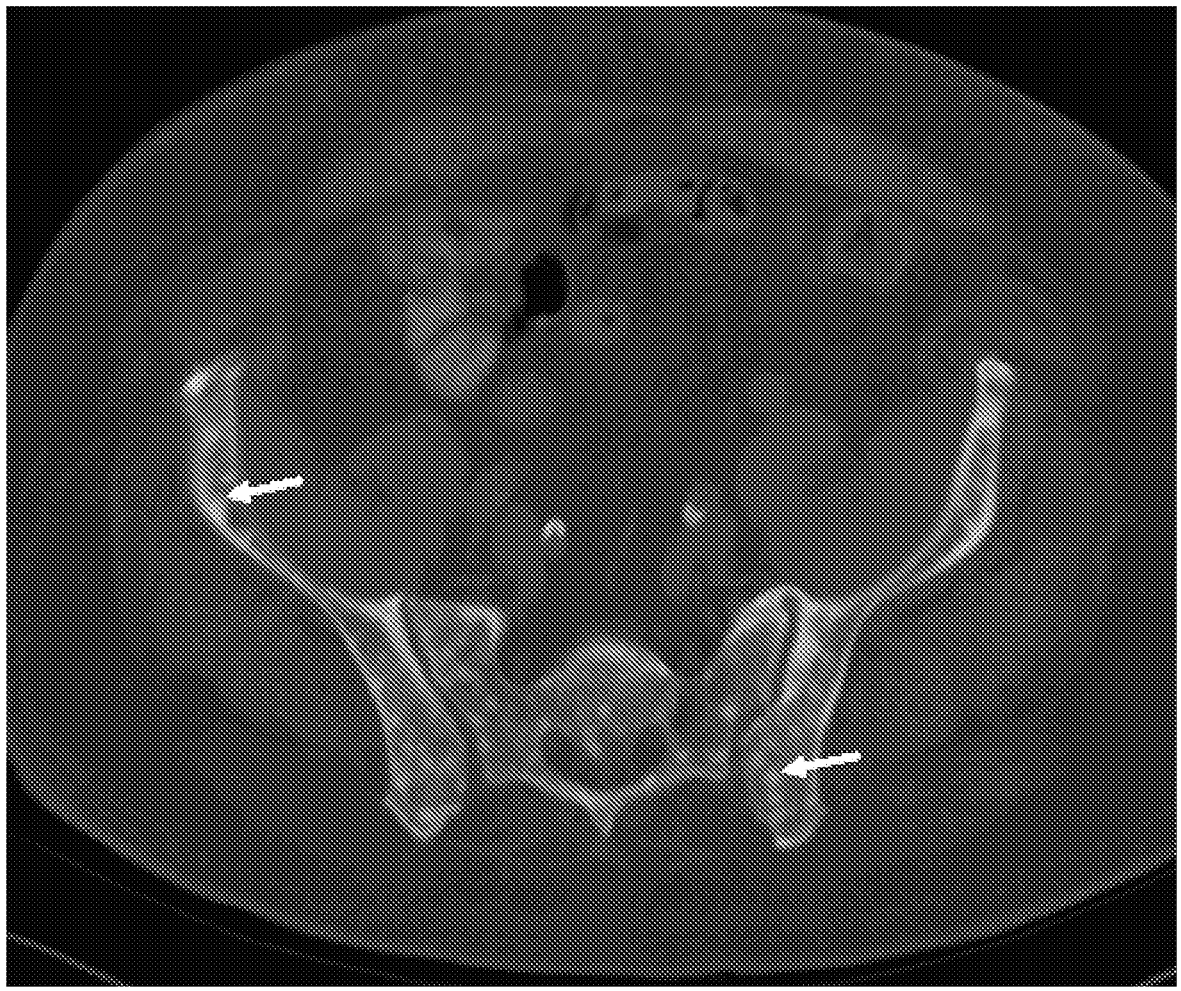
FIG. 11 shows a sample axial CT image of the pelvis in bone window. Note the flagged blastic medullary lesion indicated in the left innominate bone with the left arrow and the flagged blastic cortical lesion indicated in the right innominate bone with the right arrow.
Figure 12:
FIG. 12 shows a sample oblique sagittal CT image of the abdomen. Note that the middle area identifies the pancreas, the left arrow identifies the adjacent bowel, and the right arrow identifies the vascular structure.
Figure 13:
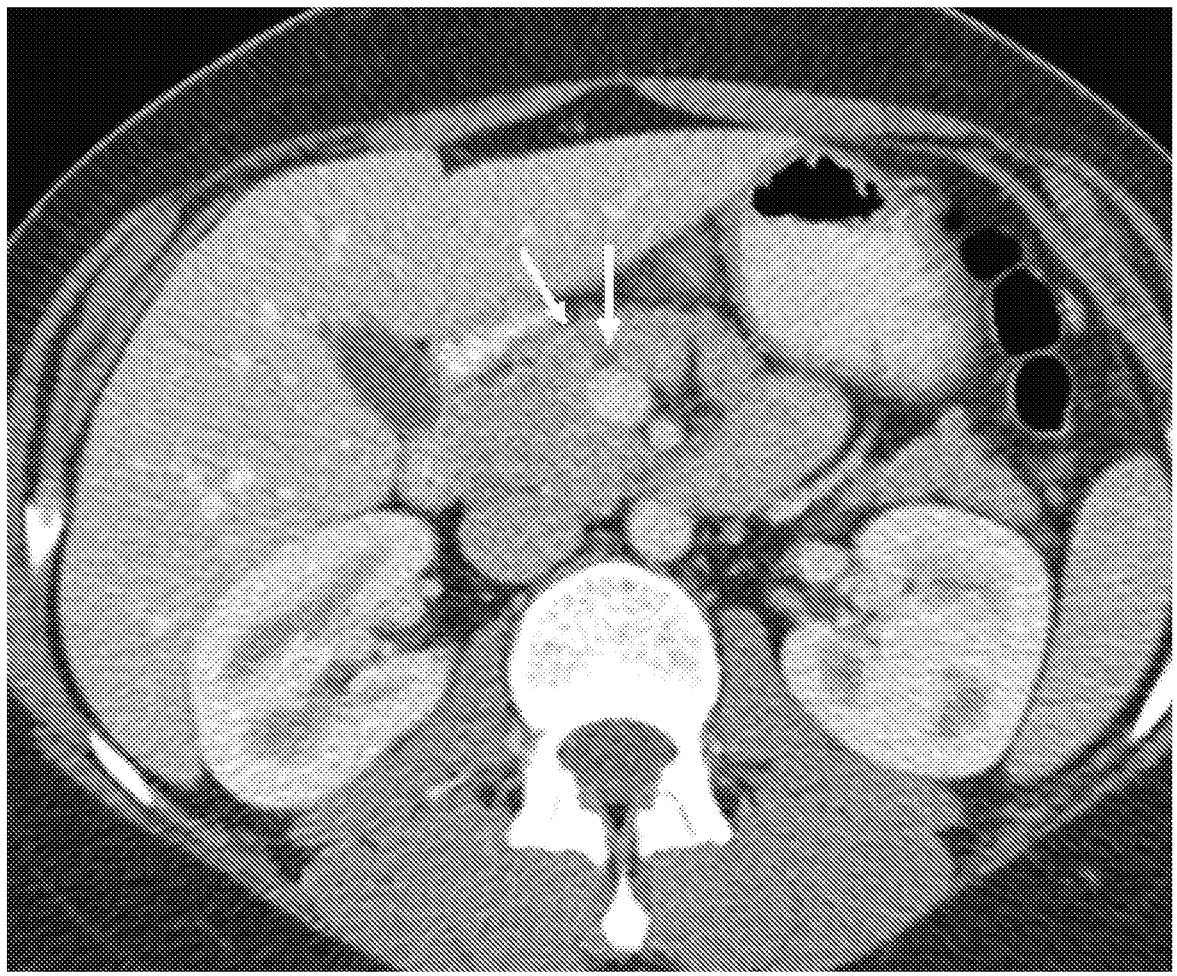
FIG. 13 shows a sample axial CT of the abdomen. Note the small cystic lesion indicated with the right arrow in the pancreatic neck with average HU lower than the background and the pancreas indicated with the left arrow.
Figure 14:
FIG. 14 shows a sample coronal CT of the abdomen. Note the mass indicated with the right arrow marked in the pancreatic wall with average HU lower than the background and the pancreas indicated with the left arrow.

FIGS. 3-5 shows a flowchart of an example methods 300, 400 and 500 determining, via the computing device 200, whether the expanded selected voxels indicate a presence of a soft tissue body, bone and/or pathologic cells and, based on that determination, modifying the digital image to include indications of the soft tissue body, bone and/or pathologic cells, according to an example implementation. Methods 300, 400 and 500 shown in FIGS. 3-5 presents an example of a method that could be used with the computing device 200 of FIG. 2, for example. Further, devices or systems may be used or configured to perform logical functions presented in FIGS. 3-5, medical imaging equipment 105 itself. In some instances, components of the devices and/or systems may be configured to perform the functions such that the components are configured and structured with hardware and/or software to enable such performance. Components of the devices and/or systems may be arranged to be adapted to, capable of, or suited for performing the functions, such as when operated in a specific manner. Methods 300, 400 and 500 may include one or more operations, functions, or actions as illustrated by one or more of blocks 305-325, 405-425 and 505-535. Although the blocks are illustrated in a sequential order, some of these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of the present examples. In this regard, each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time such as register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block in FIGS. 3-5, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

III. Example Methods

The following examples relate to the detection of soft tissue bodies, bone and pathologic cells, including lymph nodes, bony lesions, and pancreatic masses that have a high likelihood of pathology. However, the non-transitory computer readable medium and methods described herein may also be used to detect other types of masses that have a high likelihood of pathology.

Referring now to FIG. 3, a method 30) is illustrated using the computing device of FIGS. 1-2. Method 300 is directed to detecting pathologic lymph nodes and includes, at block 305, the computing device receives a digital image, where the image comprises a plurality of voxels. The computing device next selects at least one voxel relating to soft tissue cells at block 310. Then, at block 315, the computing device expands the selected voxels to include adjacent voxels until an endpoint voxel is identified. The computing device then determines whether the expanded selected voxels indicate a presence a soft tissue body, at block 320. Based on the determination that the expanded selected voxels indicate the presence of pathologic cells, the computing device associates the digital image with a database of digital images showing soft tissue bodies, at block 325.

In one embodiment, the method 300 also includes the computing device modifying the digital image to include indications of the presence of the soft tissue body based on the determination that the expanded selected voxels indicate the presence of the soft tissue body.

In another embodiment, the method 300 further includes the computing device determining whether the expanded selected voxels indicate a presence of pathologic cells. Then, based on a determination that the expanded selected voxels indicate the presence of pathologic cells, the computing device modifies the image to include indications of the pathologic cells.

Method 400, shown in FIG. 4, is directed to detecting bone metastasis using the computing device of FIGS. 1-2 and includes, at block 405, the computing device receiving a digital image, where the digital image comprises a plurality of voxels. At block 410, the computing device then selects at least one voxel relating to a bone cell. Next, at block 415, the computing device expands the selected voxels to include adjacent voxels until an endpoint voxel is identified. Then the computing device determines whether the expanded selected voxels indicate a presence of a bone, at block 420. Based on the determination that the expanded selected voxels indicate the presence of pathologic cells, the computing device associates the digital image with a database of digital images showing bones.

In one embodiment, the method 400 includes the computing device modifying the digital image to include indications of the bone based on a determination that the expanded selected voxels indicate the presence of the bone.

In a further embodiment, the method 400 further includes the computing device determining whether the expanded selected voxels indicate a presence of pathologic cells. Then, based on the determination that the expanded selected voxels indicate the presence of pathologic cells, the computing device modifies the digital image to include indications of the pathologic cells.

Method 500, shown in FIG. 5, is directed to detecting pancreatic masses using the computing device of FIGS. 1-2 and includes, at block 505, the computing device receiving a digital image, where the digital image includes a plurality of voxels. Then, at block 510, either the user or the computing device identifies at least one vascular structure within the plurality of voxels. Next, at block 515, either the user or the computing device excludes the at least one vascular structure from the plurality of voxels. At block 520, the computing device selects at least one voxel relating to a soft tissue cell. The computing device expands the selected voxels to include adjacent voxels until an endpoint voxel is identified, at block 525. Then, at block 530, the computing device determines whether the expanded selected voxels indicate a soft tissue body. Based on the determination that the expanded selected voxels indicate the presence of the soft tissue body, the computing device then associates the digital image with a database of digital images showing soft tissue bodies, at block 535.

In one optional embodiment, the method 500 further includes the computing device modifying the digital image to include indications of the soft tissue body based on a determination that the expanded selected voxels indicate the presence of the soft tissue body.

In another optional embodiment, the method 500 includes the computing device determining whether the expanded selected voxels indicate a presence of pathologic cells. And then, based on a determination that the expanded selected voxels indicate the presence of the pathologic cells, the computing device modifies the digital image to include indications of the pathologic cells.

The non-transitory computer-readable medium, described below, that has stored thereon program instructions that upon execution by a processor 202 may be utilized to cause performance of any of the functions of the foregoing methods. And the methods 300, 400 and 500 may include any of the set of acts described below with respect to the computer-readable medium.

IV. Example Computer-Readable Medium

Soft Tissue Cells—Lymph Nodes

One example non-transitory computer-readable medium is disclosed that has stored thereon program instructions that upon execution by a processor 202, cause performance of a set of acts that include receiving a digital image, where the image comprises a plurality of voxels. The processor 202 then selects from the plurality of voxels at least one voxel corresponding to soft tissue cells. Next the processor 202 expands the selected voxels to include adjacent voxels until an endpoint voxel is identified. Then the processor 202 determines whether the expanded selected voxels indicate a presence of a soft tissue body. In response to a determination that the expanded selected voxels indicate the presence of the soft tissue body, the processor 202 associates the digital image with a database of digital images showing soft tissue bodies.

In one optional embodiment, the processor 202 modifies the digital image to include indications of the presence of the soft tissue body in response to the determination that the expanded selected voxels indicate the presence of the soft tissue body. In one optional embodiment, the processor 202 modifying the digital image to include indications of the presence of the soft tissue body, includes coloring the expanded selected voxels that correspond to the soft tissue body. In another optional embodiment, the processor 202 modifying the digital image to include indications of the presence of the soft tissue body, includes adding at least one indicator to call out the expanded selected voxels that correspond to the soft tissue body on the modified image.

In another optional embodiment, the processor determines whether the expanded selected voxels indicate a presence of pathologic cells. Then, in response to a determination that the expanded selected voxels indicate the presence of the pathologic cells, the processor 202 modifies the digital image to include indications of the pathologic cells. In one optional embodiment, the processor 202 modifying the digital image to include indications of pathologic cells includes coloring the expanded selected voxels on the modified image. In another embodiment, the processor 202 modifying the digital image to include indications of pathologic cells includes adding an indicator to call out the expanded selected voxels on the modified image.

In one optional embodiment, the digital image is a Digital Imaging and Communications in Medicine (DICOM) compliant image. In a further embodiment, the DICOM compliant image includes a computed tomography (CT) image. In another embodiment, the DICOM compliant image is in a Neuroimaging Informatics Technology Initiative (NiFTI) file format.

In one optional embodiment, the processor 202 selecting from the plurality of voxels at least one voxel corresponding to soft tissue cells includes excluding voxels corresponding to cells for one or more of bone, metal, air, and fat. In another optional embodiment, the processor selecting from the plurality of voxels at least one voxel corresponding to soft tissue cells includes excluding voxels from the selected voxels based on a spatial relation to a branched object. The spatial relation may be a 6-connectivity to at least one of the selected voxels, an 18-connectivity to at least one of the selected voxels, or a 26-connectivity to at least one of the selected voxels. In addition, the branched object includes an aorta, a portal vein, and/or a systemic vein.

In another optional embodiment, the processor 202 selecting from the plurality of voxels at least one voxel corresponding to soft tissue cells includes selecting a group of voxels lacking a defined border. The group of voxels lacking a defined border may include a pathologic lymph node.

In one optional embodiment, the processor 202 expanding the selected voxels to include adjacent voxels until an endpoint voxel is identified includes determining a Hounsfield unit for an adjacent voxel to one of the selected voxels. And in response to determining that the Hounsfield unit range is between 10 and 145, then the processor 202 identifies the adjacent voxel as the endpoint voxel. The endpoint voxel includes a voxel corresponding to fat or bone. In an alternative embodiment, the endpoint voxel includes a voxel corresponding to a branched object. In a further embodiment, the identification of the endpoint voxel occurs after expansion of the selected voxels to include adjacent voxels having a diameter ranging from 0.1 mm to 100 mm. In another embodiment, the identification of the endpoint voxel occurs after expansion of the selected voxels to include adjacent voxels having a volume of about 0.01 mL to 100 mL.

In one optional embodiment, the processor 202 determining whether the expanded selected voxels indicate the presence of pathologic cells includes applying a probability analysis that includes at least one parameter. The at least one parameter may include a short-axis diameter of the expanded selected voxels exceeds 10 mm. In another embodiment, the at least one parameter includes a short-axis diameter of the expanded selected voxels. In this instance, the processor 202 determines that the short-axis diameter of the soft tissue body exceeds 5 mm and determines that the expanded selected voxels are located in an anatomic site near a rectum. Alternatively, the at least one parameter may be based on the endpoint voxel. In other embodiments, the at least one parameter include, but are not limited to, a radionomic quality, such as size (e.g., cortical thickness, volume, surface area, circumference), density composition, attenuation, signal characteristics, enhancement (e.g., pre- vs. post-contrast), and margins (e.g., geometric center).

In one optional embodiment, the non-transitory computer-readable medium further includes the processor 202 receiving feedback from a medical provider. The feedback includes adjustments to the indications of pathologic cells on the modified image. In further embodiment, the non-transitory computer-readable medium further includes the processor 202 incorporating the feedback into the determination of whether the expanded selected voxels indicate the presence of pathologic cells.

In one optional embodiment, the non-transitory computer-readable medium further includes identifying surrounding voxels to the expanded selected voxels. In a further embodiment, the non-transitory computer-readable medium further includes the processor 202 determining whether the surrounding voxels form a substantially spherical or substantially lobed shape. In a further embodiment, the processor 202 determining whether the surrounding voxels form a substantially spherical or substantially lobed shape includes determining that a ratio of a long-axis diameter of the surrounding voxels to a short-axis diameter of the surrounding voxels is less than 2.

In one optional embodiment, the non-transitory computer-readable medium further includes the processor 202 determining the existence of a cluster of expanded selected voxels. This determination includes the processor 202 repeating the selection and expansion of the plurality of voxels corresponding to soft tissue cells to determine a plurality of expanded selected voxels. And the processor 202 determines that a proximity between each of the plurality of expanded selected voxels is 12 cm or less.

In one optional embodiment, the non-transitory computer-readable medium further includes the processor 202 transmitting four to ten modified images for every thousand received digital images.

Example—Lymph Node Detection

The computer-readable medium and methods described herein may relate to the detection of lymph nodes that have a high likelihood of pathology. The systems and methods may utilize medical CT or PET images, for example, from a patients neck, thoracic, abdomen, pelvis, and abdomino-perineal regions.

Voxel Selection

A benefit of the disclosure is to identify voxels primarily in the soft tissue range. Voxels may relate to a plurality of cells, potentially millions of cells. This may be achieved by excluding voxels pertaining to other aspects of the body. In addition, engaging in an exclusionary phase for all voxels in the dataset decreases unnecessary iterations. Specifically, exclusion of voxels may be based on structure density such that voxels corresponding to Hounsfield Unit (HU) ranges for bone, metal, air, and fat density are excluded. Additionally or alternatively, exclusion may occur when voxels create objects outside of the size ranges based on the diameters and volumes indicated below. Exclusion may also be based on spatial relation to a branched object thereby permitting voxels within vasculature to be excluded as well.

Object Creation

Once voxels have been selected and excluded, the selected voxels are analyzed as they form the nidus for a possible pathologic object. These selected voxels are marshalled in a scanning cranial to caudal orientation. The origin voxel then undergoes growth of adjacent voxels based on soft tissue attenuation and/or density in a known Hounsfield range. Voxel expansion of the selected voxels may continue until 1) a Hounsfield unit for an adjacent voxel to one of the selected voxels ranges from 10 HU and 145 HU, 2) a voxel is identified that corresponds to fat, bone, or branched structures and 3) the average diameter of the selected voxels is about 0.1 mm to 100 mm or the volume of the selected voxel is about 0.01 to 100 mL. In alternative embodiments, a Hounsfield unit for an adjacent voxel to one of the selected voxels may range from 0 HU to 180 HU or from −20 HU to 250 HU. Any voxels within the currently created object could then be excluded from the unprocessed voxel queue as object characteristics should be transitive.

Object Characterization

The expanded selected voxels (e.g., created objects) would then be selected for output if they indicated the presence of pathologic cells. To determine whether there is a presence of pathologic cells, the processor may apply a probability analysis that includes at least one parameter. Parameters may include a short-axis diameter of the expanded selected voxels and the voxel classification of the endpoint voxels. Initial ranges for these parameters would be prescribed, however, machine learning based on a feedback loop from human expert interaction and/or an imported data set (i.e., The National Institute of Health's CT dataset) would allow for regional and/or practice variations and output optimization.

Output

The output phase of the method renders an indication that may be user-customized and overlaid onto the digital images via PACS, for example. These indications may be in the form of coloring, markings (i.e., shapes, asterisks, etc.), and/or a set of coordinates on the image. The indicators may refer medical personnel to lymph nodes that have a high likelihood of pathology.

Bone Cell—Bone Metastasis

In another aspect of the disclosure, a non-transitory computer-readable medium is provided having stored thereon program instructions that upon execution by a processor 202, cause performance of a set of acts that include receiving a digital image, where the digital image includes a plurality of voxels. The processor 202 then selects from the plurality of voxels at least one voxel corresponding to a bone cell. Next, the processor 202 expands the selected voxels to include adjacent voxels until an endpoint voxel is identified. The processor 202 then determines whether the expanded selected voxels indicate a presence of a bone. And, in response to a determination that the expanded selected voxels indicate the presence of the soft tissue body, the processor 202 associates the digital image with a database of digital images showing bones.

In one optional embodiment, the processor 202 modifies the digital image to include at least one indication of the presence of the bone in response to a determination that the expanded selected voxels indicate the presence of the bone. In a further embodiment, the processor 202 modifying the digital image to include indications of the presence of the bone, includes coloring the expanded selected voxels that correspond to the bone. In another optional embodiment, the processor 202 modifying the digital image to include indications of the presence of the bone, includes adding at least one indicator to call out the expanded selected voxels that correspond to the bone on the modified image.

In another optional embodiment, the processor 202 determines whether the expanded selected voxels indicate a presence of pathologic cells. Then, in response to a determination that the expanded selected voxels indicate the presence of the pathologic cells, the processor 202 modifies the digital image to include indications of the pathologic cells. In one optional embodiment, the processor 202 modifying the digital image to include indications of pathologic cells includes coloring the expanded selected voxels on the modified digital image. Alternatively or in addition, the processor 202 modifying the digital image to include indications of pathologic cells includes adding an indicator to call out the expanded selected voxels on the modified digital image.

In one optional embodiment, the digital image is a Digital Imaging and Communications in Medicine (DICOM) compliant image. In another embodiment, the DICOM compliant image includes a computed tomography (CT) image. In still another embodiment, the DICOM compliant image is in a Neuroimaging Informatics Technology Initiative (NiFTI) file format.

In another optional embodiment, the processor 202 selecting from the plurality of voxels at least one voxel corresponding to a bone cell includes excluding voxels corresponding to cells for one or more of soft tissue, metal, air, and fat. In another embodiment, the processor 202 selecting from the plurality of voxels at least one voxel corresponding to a bone cell includes excluding voxels with a cortical thickness of about 0.5 mm to about 15 mm. In an alternative embodiment, the processor 202 selecting from the plurality of voxels at least one voxel corresponding to a bone cell includes excluding voxels with an average thickness of about 1 mm to about 6 mm. In still another embodiment, the processor 202 selecting from the plurality of voxels at least one voxel corresponding to a bone cell includes excluding voxels with a standard deviation of thickness of less than about 0.5 mm to about 3 mm. In yet another embodiment, the processor 202 selecting from the plurality of voxels at least one voxel corresponding to a bone cell comprises excluding voxels with an average diameter greater than about 10 mm to about 100 mm.

In one optional embodiment, the endpoint voxel includes a voxel corresponding to cortical bone. In another embodiment, the identification of the endpoint voxel occurs after expansion of the selected voxels to include adjacent voxels having a diameter range of about 1 mm to about 15 mm. In an alternative embodiment, the identification of the endpoint voxel occurs after expansion of the selected voxels to include adjacent voxels having a volume of about 0.1 mL to about 50 mL.

In another optional embodiment, the processor 202 determining whether the expanded selected voxels indicate the presence of pathologic cells includes applying a probability analysis that includes at least one parameter. In a further embodiment, the at least one parameter includes an average diameter of the expanded selected voxels. In another embodiment, the at least one parameter includes an average Hounsfield unit of the expanded selected voxels. In still another embodiment, the at least one parameter includes a standard deviation of Hounsfield unit values of the expanded selected voxels. In other embodiments, the at least one parameter include, but are not limited to, a radionomic quality, such as size (e.g., cortical thickness, volume, surface area, circumference), density composition, attenuation, signal characteristics, enhancement (e.g., pre- vs. post-contrast), and margins (e.g., geometric center).

In one optional embodiment, the computer-readable medium includes the processor 202 receiving feedback from a medical provider. That feedback includes adjustments to the indications of pathologic cells on the modified digital image. In a further embodiment, the computer-readable medium further includes the processor 202 incorporating the feedback into the determination of whether the expanded selected voxels indicate the presence of pathologic cells.

In another optional embodiment, the computer-readable medium further includes the processor 202 transmitting four to ten modified images for every thousand received digital images.

Example—Bone Metastasis

The computer-readable medium and methods described above may also be applied to the detection of bone metastasis. Similar to the detection of lymph nodes, the computer-readable medium and methods may use medical CT or PET images from a patient's axial or appendicular skeleton.

Extending the systems and methods to detection of bone metastasis may allow for the creation of imaging objects that correlate to bony lesions that have a high likelihood of pathology.

Voxel Selection

Another benefit of the disclosure is to identify voxels that correlate to cortical bone. This may be achieved by excluding voxels pertaining to other aspects of the body (e.g., voxels that correlate to soft tissue). Specifically, exclusion of voxels may be based on structure density such that voxels corresponding to Hounsfield ranges for metal, air, and fat density are included. A reference range of about 150 HU to about 3000 HU may be used to parse the voxels for exclusion.

Bone Object Creation

Once the voxels have been selected and excluded, the selected voxels are analyzed for cortical thickness (i.e., maximum, average, minimum, and standard deviation of thickness), average diameter, and maximum length. Voxels having a cortical thickness ranging from about 0.5 mm to about 15 mm, average thickness of about 1 mm to about 6 mm, standard deviation of thickness of less than about 0.5 mm to about 3 mm, overall length greater than about 10 mm to about 400 mm, or average diameter greater than about 10 mm to about 100 mm are then excluded as they correlate to non-bony calcified material.

Voxel Inclusion

After the bony object is created, voxels are selected for analysis. The voxels are separated into two groups; (i) cortical bone and (ii) medullary bone. All the voxels used to create the bony objects, except for the voxels excluded as non-bony calcified material, would be analyzed as cortical bone. Additionally, all the voxels demarcated by the internal/closed volumetric region within the created bony objects may be classified as medullary bone and analyzed accordingly. The average and standard deviation HU for all medullary bone spaces may then be calculated for reference.

Object Creation

First, object creation is applied to the voxels classified as medullary bone. The origin voxel undergoes growth of adjacent voxels until endpoints are reached, which may include 1) margination by cortical bone voxels, 2) the average diameter of the object is about 1 mm to about 15 mm and the volume is about 0.1 mL to about 5 mL. Voxel growth may happen in a stepwise lamelliform fashion. Once a particular object size is met (e.g., average diameter of about 0.5 mm to about 3 mm and volume of about 0.1 mL to about 0.5 mL), the average diameter, volume, average HU, and standard deviation of HU, is calculated after every voxel addition. When a created object deviates from having certain characteristics, the object may be entered into the object characterization queue. The characteristics may include having soft tissue (i.e., about 0 HU to about 100 average HU), blastic bony masses (i.e., about 10 HU to about 3000 average HU), relative reduction (negative variance) of standard deviation HU from a patient's baseline (i.e., about −0.5 to about −15), and/or an absolute standard deviation HU value (i.e., about 1 HU to about 10 HU). During growth of adjacent voxels, only a single object would be entered into the object characterization queue. The largest volume object meeting the characteristic variation criteria above would be saved into the characterization queue, and previous smaller versions would be removed. Any voxels within the currently created object would remain within the unprocessed voxel queue as object characteristics would not be transitive.

Second, object creation is applied to the voxels classified as cortical bone. A geometric center and central axis of the bony object may be generated. The origin voxel is then referenced to the closest point along the central axis or geometric center, whichever is shorter. Connected voxels (6-, 18-, and 26-connected) are then compared in a polar coordinate system. Any connected voxels that have a cortical bone HU range, and have a radius of 1 to 3 voxel width, an azimuth of 0 to 360 degrees, and an altitude of −90 to 90 degrees, are considered to have satisfactory characteristics and are included into the created object. The connected voxels that do not have a cortical bone HU range are counted and used to form an object for characterization.

When analyzing the created object, a sufficient number (i.e., 1 to 5000) of "empty" connected bony voxels would represent a non-physiologic bony edge (lytic disease). Next detection of blastic cortical lesions would occur. Voxels within focal cortical thickening, relative increased cortical thickness (thickness >1 mm to 10 mm), would be sent for characterization.

Object Characterization

After the objects are created, they are selected for output based on a multi-parametric probability analysis. For medullary objects or lesions, parameters would include average diameter, average HU, and standard deviation HU. Medullary objects that share voxels would be conjoined and sent to the output phase as a single object or lesion. For cortical objects or lesions, parameters would include total number, clustering, and connectedness of free edge voxels. Voxels within focal cortical thickening would be flagged, allowing for maximum cortical thickness, volume of thickened cortex, and change in average/standard deviation HU of the thickened region. Initial ranges for output inclusion would be prescribed, however machine learning based on human expert interaction and/or imported data sets would allow for regional and/or practice variations and output optimization.

Output

The output phase of the method renders an indication that may be user-customized and overlaid onto the digital images via PACS, for example. These indications may be in the form of coloring, markings (i.e., shapes, asterisks, etc.), and/or a set of coordinates on the image. The indicators may refer medical personnel to bony lesions that have a high likelihood of pathology.

Soft Tissue Cell—Pancreatic Mass

In another aspect of the disclosure, another example non-transitory computer-readable medium is disclosed that has stored thereon program instructions that upon execution by a processor 202, cause performance of a set of acts that include receiving a digital image, where the digital image comprises a plurality of voxels. Then the processor 202 identifies at least one vascular structure within the plurality of voxels. Next the processor 202 excludes the at least one vascular structure from the plurality of voxels. The processor then selects from the plurality of voxels at least one voxel corresponding to a soft tissue cell. The process then expands the selected voxels to include adjacent voxels until an endpoint voxel is identified. Next the processor 202 determines whether the expanded selected voxels indicate a presence of a soft tissue body. And in response to a determination that the expanded selected voxels indicate the presence of pathologic cells, the processor 202 associates the digital image with a database of digital images showing soft tissue bodies.

In one optional embodiment, in response to the determination that the expanded selected voxels indicate the presence of the soft tissue body, modifying the digital image to include at least one indication of the soft tissue body. In another optional embodiment, the processor 202 modifying the digital image to include indications of the presence of the soft tissue body, includes coloring the expanded selected voxels that correspond to the soft tissue body. In a further optional embodiment, the processor 202 modifying the digital image to include indications of the presence of the soft tissue body, includes adding at least one indicator to call out the expanded selected voxels that correspond to the soft tissue body on the modified image.

In another optional embodiment, the processor 202 determines whether the expanded selected voxels indicate a presence of pathologic cells. Then, in response to a determination that the expanded selected voxels indicate the presence of the pathologic cells, the processor 202 modifies the digital image to include at least one indication of the pathologic cells. In one optional embodiment, the processor 202 modifying the digital image to include indications of pathologic cells includes coloring the expanded selected voxels on the modified digital image. In another embodiment, the processor 202 modifying the digital image to include indications of pathologic cells includes adding an indicator to call out the expanded selected voxels on the modified digital image.

In one optional embodiment, the digital image is a Digital Imaging and Communications in Medicine (DICOM) compliant image. In a further embodiment, the DICOM compliant image comprises a computed tomography (CT) image. In another embodiment, the DICOM compliant image is in a Neuroimaging Informatics Technology Initiative (NiFTI) file format.

In one optional embodiment, the processor 202 identifying the at least one vascular structure within the plurality of voxels includes the processor 202 parsing the plurality of voxels for one or more voxels corresponding to an aorta, a portal vein, and/or a systemic vein. In a further embodiment, the processor 202 excluding the at least one vascular structure from the plurality of voxels includes removing the one or more voxels corresponding to the aorta, the portal vein, and/or the systemic vein from the plurality of voxels.

In another optional embodiment, the processor 202 selecting from the plurality of voxels at least one voxel corresponding to a soft tissue cell includes excluding voxels corresponding to cells for one or more of fat and bone. In another embodiment, the processor 202 selecting from the plurality of voxels at least one voxel corresponding to a soft tissue cell includes excluding voxels from the selected voxels based on a spatial relation to a vascular object. In various optional embodiments, the spatial relation is a 6-connectivity to at least one of the selected voxels, an 18-connectivity to at least one of the selected voxels, and a 26-connectivity to at least one of the selected voxels. In another embodiment, the processor 202 selecting from the plurality of voxels at least one voxel corresponding to a soft tissue cell includes excluding voxels from the selected voxels that correspond to a bowel.

In one optional embodiment, the endpoint voxel includes a voxel corresponding to fat. Alternatively, the endpoint voxel includes a voxel corresponding to a vascular object. Still further, the endpoint voxel may include a voxel corresponding to a bowel object. In a further embodiment, the identification of the endpoint voxel occurs after expansion of the selected voxels to include adjacent voxels having a diameter range of about 1 mm to about 30 mm and a volume of about 0.1 mL to about 15 mL.

In one optional embodiment, the processor determining whether the expanded selected voxels indicate the presence of pathologic cells includes applying a probability analysis comprising at least one parameter. In a further embodiment, the at least one parameter includes a central-axis length of the expanded selected voxels. In another embodiment, the at least one parameter is based on an average Hounsfield unit value of the expanded selected voxels. In still another embodiment, the at least one parameter is based on a standard deviation of Hounsfield unit values of the expanded selected voxels. In a further embodiment, the at least one parameter is based on a distance of one of the expanded selected voxels to a left hemi-diaphragm. In other embodiments, the at least one parameter include, but are not limited to, a radionomic quality, such as size (e.g., cortical thickness, volume, surface area, circumference), density composition, attenuation, signal characteristics, enhancement (e.g., pre- vs. post-contrast), and margins (e.g., geometric center).

In one optional embodiment, the computer-readable medium further includes the processor 202 receiving feedback from a medical provider. That feedback includes adjustments to the at least one indication of pathologic cells on the modified digital image. In another embodiment, the computer-readable medium further includes the processor 202 incorporating the feedback into the determination of whether the expanded selected voxels indicate the presence of pathologic cells.

In one optional embodiment, the computer-readable medium further includes transmitting four to ten modified images for every thousand received digital images.

Example—Pancreatic Masses

The systems and methods described above may also be applied to the detection of pancreatic masses. Similar to the detection of lymph nodes, the computer-readable medium and methods may use medical CT or PET images from a patient's abdomen.

Extending the systems and methods to detection of pancreatic masses may allow for the creation of imaging objects that correlate to pancreatic lesions that have a high likelihood of pathology.

Pancreatic Segmentation

Before voxels are selected, vascular structures are identified. All branched objects are demarcated using a scanning voxel growth technique of voxel groups in the enhanced vascular ranges, when applicable. For example, a range of about 90 HU to about 600 HU corresponds to an aorta, a range of about 70 HU to about 300 HU corresponds to a portal vein, and a range of about 70 HU to about 300 HU corresponds to a systemic vein or inferior vena cava. The length of 3D central axis (i.e., about 30 mm to about 1200 mm), average HU, standard deviation HU (i.e., about 5 HU to about 20 HU) and branchedness by single plane test may also be used in conjunction with the scanning voxel growth technique to confirm vascular object status. All remaining non-soft tissue voxels (less than about −10 HU to about 20 HU, and greater than about 90 HU to about 200 HU) from the 3D dataset would be excluded from analysis to remove unnecessary iterations. Next, soft tissue voxels would be marshalled for analysis in a scanning cranial to caudal fashion. The origin voxel would undergo growth of connected voxels if the voxel has a soft tissue HU. Son tissue voxel growth endpoints would include 1) margination by fat or bone or 2) margination by a vascular object.

This process may create numerous soft tissue objects of which the pancreas would be included. The voxel growth technique however would also include adjacent bowel objects which would need to be excluded for analysis of the pancreas. Signature bowel characteristics include: a short axis diameter (i.e., about 5 mm to about 60 mm), presence of air HU about central axis (−1000 HU), presence of confluent fluid HU about the central axis (i.e., about −15 HU to about 15 HU), presence of confluent positive oral contrast about the central axis (i.e., about 200 HU to about 600 HU), and soft tissue wall thickness of about 0.5 mm to about 9 mm. The bowel object would then be excluded for analysis of the pancreas. Selection of the pancreatic object would be achieved through multi-parametric analysis, including parameters such as length of central axis (i.e., about 12 cm to about 18 cm), average HU (i.e., about 40 HU to about 85 HU), standard deviation (i.e., about 10 HU to about 50 HU), and shortest distance within any voxel of the object to the left hemi-diaphragm (i.e., about 0 cm to about 10 cm).

Voxel Selection

After the pancreas is segmented, voxel selection occurs. All voxels along the surface of, and in the internal/closed volume of, the pancreatic object are selected for analysis.

Object Creation

The selected voxels would then be the nidus for a possible pathologic object and marshalled in a scanning cranial to caudal orientation. The index voxel would undergo growth of adjacent voxels in stepwise lamelliform fashion. This growth continues until endpoints are reached. These endpoints may include 1) margination by fat, 2) margination by vascular structure, 3) margination by bowel, 4) the overall size of the object (i.e., average diameter of about 1 mm to about 30 mm and volume of about 0.1 mL to about 15 mL). Once the object has an average diameter of about 0.5 mm to about 3 mm and volume of about 0.1 mL to about 0.5 mL, every additional voxel will trigger a calculation of average diameter, volume, average HU, and standard deviation HU for the created object. Deviation of expected characteristics then triggers the object to enter the object characterization queue for characterization. The expected characteristics include soft tissue average HU (i.e., about 0 HU to about 100 HU), relative change of standard deviation HU from a pancreatic baseline (i.e., about −15 HU to about 15 HU), and absolute standard deviation HU value (i.e., about 1 HU to about 10 HU). During growth of adjacent voxels, only a single object would be entered into the object characterization queue. The largest volume object meeting the characteristic deviation criteria would be saved into the characterization queue, with smaller objects being removed. Any voxels within the currently created object would remain within the unprocessed voxel queue as object characteristics are not transitive.

Object Characterization

Created objects are then selected for output based on multi-parametric probability analysis. Parameters can include average diameter, average HU, and standard deviation HU. Objects that share voxels are conjoined and sent to the output phase as a single object or lesion. Initial ranges for output inclusion would be prescribed, however machine learning based on human expert interaction and/or imported data sets would allow for regional and/or practice variations and output optimization.

Output

The output phase of the method renders an indication that may be user-customized and overlaid onto the digital images via PACS, for example. These indications may be in the form of coloring, markings (i.e., shapes, asterisks, etc.), and/or a set of coordinates on the image. The indicators may refer medical personnel to bony lesions that have a high likelihood of pathology.

Extension to MRI

The computer-readable medium and methods described above may also be extended to magnetic resonance imaging ("MRI"). In the extension to MRI, the computer-readable medium and methods may use data obtained from several MRI sequence types. The systems and methods may use primary datasets or derived or multi-parametric datasets such as diffusion-weighted imaging ("DWI") or dynamic contrast-enhanced ("DCE") MRI.

In the extension to MRI, the computer-readable medium and methods would instead select voxels based on their intensity. The expansion of voxels from the origin voxel to the 6-, 18-, or 26-connected neighboring voxels would not be the same, instead determining growth extent based on intensity. The probabilistic determination of end-point would be of similar nature to that of CT. As in CT, initial ranges for these parameters would be prescribed, however, machine learning based on a feedback loop from human expert interaction and/or imported data sets would allow for regional and/or practice variations and output optimization.

In the extension to MRI, the systems and methods may still use DICOM but may also use the NIfTI-1 (.nii) file format, an extension of the ANALYZE 7.5 file format. NIfTI-1 datasets contain the same voxel information as DICOM but have a reduced header to accommodate the spatial information relevant to the study. NIfTI-1 datasets are most common to functional MRI (fMRI) but may be extended to general MRI datasets.

The description of different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A non-transitory computer-readable medium having stored thereon program instructions that upon execution by a processor, cause performance of a set of acts comprising:
   receiving a digital image, wherein the image comprises a plurality of voxels;
   selecting from the plurality of voxels at least one voxel corresponding to soft tissue cells;
   expanding the selected voxels to include voxels adjacent to the selected voxels repeatedly until an endpoint voxel is identified;
   determining whether the expanded selected voxels indicate a presence of a soft tissue body; and
   in response to a determination that the expanded selected voxels indicate the presence of the soft tissue body, associating the digital image with a database of digital images showing soft tissue bodies.

2. The non-transitory computer-readable medium of claim 1, further comprising:
   in response to the determination that the expanded selected voxels indicate the presence of the soft tissue body, modifying the digital image to include indications of the presence of the soft tissue body.

3. The non-transitory computer-readable medium of claim 1, further comprising:
   determining whether the expanded selected voxels indicate a presence of pathologic cells; and
      in response to a determination that the expanded selected voxels indicate the presence of the pathologic cells, modifying the digital image to include indications of the pathologic cells.

4. The non-transitory computer-readable medium of claim 1, wherein the digital image is a Digital Imaging and Communications in Medicine (DICOM) compliant image.

5. The non-transitory computer-readable medium of claim 4, wherein the DICOM compliant image comprises a computed tomography (CT) image or wherein the DICOM compliant image is in a Neuroimaging Informatics Technology Initiative (NiFTI) file format.

6. The non-transitory computer-readable medium of claim 1, wherein selecting from the plurality of voxels at least one voxel corresponding to soft tissue cells comprises (a) excluding voxels corresponding to cells for one or more of bone, metal, air, and fat, or (b) excluding voxels from the selected voxels based on a spatial relation to a branched object; and optionally wherein the spatial relation is a 6-connectivity to at least one of the selected voxels, an 18-connectivity to at least one of the selected voxels, or a 26-connectivity to at least one of the selected voxels, and optionally wherein the branched object comprises an aorta, a portal vein, and/or a systemic vein.

7. The non-transitory computer-readable medium of claim 1, wherein selecting from the plurality of voxels at least one voxel corresponding to soft tissue cells comprises selecting a group of voxels lacking a defined border, optionally wherein the group of voxels lacking a defined border comprises a lymph node.

8. The non-transitory computer-readable medium of claim 1, wherein expanding the selected voxels to include voxels adjacent to the selected voxels repeatedly until an endpoint voxel is identified comprises:
   determining a Hounsfield unit for an voxel adjacent to one of the selected voxels; and
   in response to determining that the Hounsfield unit range is between 10 and 145, identifying the adjacent voxel as the endpoint voxel.

9. The non-transitory computer-readable medium of claim 1, wherein the endpoint voxel comprises a voxel corresponding to fat or bone; or wherein the endpoint voxel comprises a voxel corresponding to a branched object.

10. The non-transitory computer-readable medium of claim 1, wherein the identification of the endpoint voxel occurs after expansion of the selected voxels to include adjacent voxels having a diameter ranging from 0.1 mm to 100 mm; or wherein the identification of the endpoint voxel occurs after expansion of the selected voxels to include adjacent voxels having a volume of about 0.01 to 100 mL.

11. The non-transitory computer-readable medium of claim 3, wherein determining whether the expanded selected voxels indicate the presence of pathologic cells comprises applying a probability analysis comprising at least one parameter.

12. The non-transitory computer-readable medium of claim 11, wherein (a) the at least one parameter comprises a short-axis diameter of the expanded selected voxels and determining that the short-axis diameter of the expanded selected voxels exceeds 10 mm; or (b) the at least one parameter comprises a short-axis diameter of the expanded selected voxels and determining that the short-axis diameter of the soft tissue body exceeds 5 mm and determining that the expanded selected voxels are located in an anatomic site near a rectum, or (c) wherein the at least one parameter is based on the endpoint voxel.

13. The non-transitory computer-readable medium of claim 2, wherein modifying the digital image to include indications of the presence of the soft tissue body, comprises coloring the expanded selected voxels that correspond to the soft tissue body; or wherein modifying the digital image to include indications of the presence of the soft tissue body, comprises adding at least one indicator to call out the expanded selected voxels that correspond to the soft tissue body on the modified image.

14. The non-transitory computer-readable medium of claim 3, wherein modifying the digital image to include indications of pathologic cells comprises coloring the expanded selected voxels that correspond to the pathologic cells on the modified image; or wherein modifying the digital image to include indications of pathologic cells comprises adding at least one indicator to call out the expanded selected voxels that correspond to the pathologic cells on the modified image.

15. The non-transitory computer-readable medium of claim 3, further comprising:
   receiving feedback from a medical provider, wherein the feedback comprises adjustments to the indications of at least one of the soft tissue body and the pathologic cells on the modified image, optionally further comprising incorporating the feedback into the determination of whether the expanded selected voxels indicate the presence of at least one of the soft tissue body and the pathologic cells.

16. The non-transitory computer-readable medium of claim 1, further comprising:
    identifying surrounding voxels to the expanded selected voxels; optionally further comprising determining whether the surrounding voxels form a substantially spherical or substantially lobed shape; and further optionally wherein determining whether the surrounding voxels form a substantially spherical or substantially lobed shape comprises determining that a ratio of a long-axis diameter of the surrounding voxels to a short-axis diameter of the surrounding voxels is less than 2.

17. The non-transitory computer-readable medium of claim 1, further comprising determining the existence of a cluster of expanded selected voxels, wherein determining the existence of a cluster of expanded selected voxels comprises:
    repeating the selection and expansion of the plurality of voxels corresponding to soft tissue cells to determine a plurality of expanded selected voxels; and
    determining that a proximity between each of the plurality of expanded selected voxels is 12 cm or less; and
    optionally, further comprising transmitting four to ten modified images for every thousand received digital images.

18. A method of detecting lymph nodes, the method comprising:
    receiving, via a computing device, a digital image, wherein the image comprises a plurality of voxels;
    selecting, via the computing device, at least one voxel relating to soft tissue cells;
    expanding, via the computing device, the selected voxels to include voxels adjacent to the selected voxels repeatedly until an endpoint voxel is identified;
    determining, via the computing device, whether the expanded selected voxels indicate a presence of a soft tissue body; and
    based on a determination that the expanded selected voxels indicate the presence of the soft tissue body, associating, by the computing device, the digital image with a database of digital images showing soft tissue bodies.

19. A non-transitory computer-readable medium having stored thereon program instructions that upon execution by a processor, cause performance of a set of acts comprising:
    (a)
    receiving a digital image, wherein the digital image comprises a plurality of voxels;
    selecting from the plurality of voxels at least one voxel corresponding to a bone cell;
    expanding the selected voxels to include voxels adjacent to the selected voxels repeatedly until an endpoint voxel is identified;
    determining whether the expanded selected voxels indicate a presence of a bone; and
    in response to a determination that the expanded selected voxels indicate the presence of the bone, associating the digital image with a database of digital images showing bones; or
    (b):
    receiving a digital image, wherein the digital image comprises a plurality of voxels;
    identifying at least one vascular structure within the plurality of voxels;
    excluding the at least one vascular structure from the plurality of voxels;
    selecting from the plurality of voxels at least one voxel corresponding to a soft tissue cell;
    expanding the selected voxels to include voxels adjacent to the selected voxels repeatedly until an endpoint voxel is identified;
    determining whether the expanded selected voxels indicate a presence of a soft tissue body; and
    in response to a determination that the expanded selected voxels indicate the presence of the soft tissue body, associating the digital image with a database of digital images showing soft tissue bodies.

20. A method
    (a) of detecting bone metastasis, the method comprising:
    receiving, via a computing device, a digital image, wherein the digital image comprises a plurality of voxels;
    selecting, via the computing device, at least one voxel relating to a bone cell;
    expanding, via the computing device, the selected voxels to include voxels adjacent to the selected voxels repeatedly until an endpoint voxel is identified;
    determining, via the computing device, whether the expanded selected voxels indicate a presence of bone; and
    based on a determination that the expanded selected voxels indicate the presence of the bone, associating, by the computing device, the digital image with a database of digital images showing bones; or
        (b) of detecting pancreatic masses, the method comprising:
    receiving, via a computing device, a digital image, wherein the digital image comprises a plurality of voxels;
    identifying at least one vascular structure within the plurality of voxels;
    excluding the at least one vascular structure from the plurality of voxels;
    selecting, via the computing device, at least one voxel relating to a soft tissue cell;
    expanding, via the computing device, the selected voxels to include voxels adjacent to the selected voxels repeatedly until an endpoint voxel is identified;
    determining, via the computing device, whether the expanded selected voxels indicate a presence of a soft tissue body; and
    based on a determination that the expanded selected voxels indicate the presence of the soft tissue body, associating, by the computing device, the digital image with a database of digital images showing soft tissue bodies.

* * * * *